United States Patent
Boyce et al.

(10) Patent No.: US 6,294,041 B1
(45) Date of Patent: Sep. 25, 2001

(54) METHOD FOR AN OSTEOIMPLANT MANUFACTURE

(75) Inventors: Todd M. Boyce, Aberdeen; Albert Manrique, Manalapan, both of NJ (US)

(73) Assignee: Osteotech, Inc., Eatontown, NJ (US)

( * ) Notice: Subject to any disclaimer, the term of this patent is extended or adjusted under 35 U.S.C. 154(b) by 0 days.

(21) Appl. No.: 09/296,845

(22) Filed: Apr. 22, 1999

Related U.S. Application Data (62) Division of application No. 09/020,205, filed on Feb. 6, 1998, now Pat. No. 6,123,731.

(51) Int. Cl.$^7$ .................................................. B32B 31/00
(52) U.S. Cl. ...................... 156/275.5; 264/430; 264/446; 623/23.63; 8/94.11
(58) Field of Search ............................. 623/11, 16, 23.63, 623/23.51, 23.56, 23.57, 23.61, 23.76; 600/36; 523/115; 8/94.11; 156/275.5; 264/430, 446

(56) References Cited

U.S. PATENT DOCUMENTS

| | | |
|---|---|---|
| 3,609,867 | 10/1971 | Hodosh . |
| 3,790,507 | 2/1974 | Hodosh . |
| 4,394,370 | 7/1983 | Jefferies . |
| 4,430,760 | 2/1984 | Smestad . |
| 4,440,750 | 4/1984 | Glowacki et al. . |
| 4,472,840 | 9/1984 | Jefferies . |
| 4,485,097 | 11/1984 | Bell . |
| 4,512,038 | 4/1985 | Alexander et al. . |
| 4,516,276 | 5/1985 | Mittelmeier et al. . |
| 4,623,553 | 11/1986 | Ries et al. . |
| 4,627,853 | 12/1986 | Campbell et al. . |
| 4,636,526 | 1/1987 | Dorman et al. . |
| 4,637,931 | 1/1987 | Schmitz . |
| 4,678,470 | 7/1987 | Nashef et al. . |
| 4,698,375 | 10/1987 | Dorman et al. . |
| 4,795,467 | 1/1989 | Piez et al. . |
| 4,842,604 | 6/1989 | Dorman et al. . |
| 4,932,973 | 6/1990 | Gendler . |
| 5,007,930 | 4/1991 | Dorman et al. . |
| 5,053,049 | 10/1991 | Campbell . |
| 5,061,286 | 10/1991 | Lyle . |
| 5,071,436 | 12/1991 | Huc et al. . |
| 5,112,354 | 5/1992 | Sires . |
| 5,236,456 | 8/1993 | O'Leary et al. . |
| 5,298,254 | 3/1994 | Prewett et al. . |
| 5,306,302 | 4/1994 | Bauer et al. . |
| 5,306,304 | 4/1994 | Gendler . |
| 5,314,476 | 5/1994 | Prewett et al. . |
| 5,356,629 | 10/1994 | Sander et al. . |
| 5,425,769 | 6/1995 | Snyders, Jr. . |
| 5,425,770 | 6/1995 | Piez et al. . |
| 5,464,439 | 11/1995 | Gendler . |

(List continued on next page.)

FOREIGN PATENT DOCUMENTS

| | | |
|---|---|---|
| 0243151 | 10/1987 | (EP) . |
| 0411925 | 2/1991 | (EP) . |
| 0693523 | 1/1996 | (EP) . |
| 96/39203 | 12/1996 | (WO) . |
| 98/00183 | 1/1998 | (WO) . |

OTHER PUBLICATIONS

Jurgensen, K., MD et al., "A New Biological Glue for Cartilage—Cartilage Interfaces: Tissue Transglutaminase*", Journal of Bone and Joint Surgery, Inc., p. 185–193 (2/97).

(List continued on next page.)

Primary Examiner—Paul B. Prebilic
(74) Attorney, Agent, or Firm—Dilworth & Barrese (57) ABSTRACT

The invention relates to an osteoimplant fabricated from a solid aggregate of bone derived elements possessing chemical linkages between their adjacent surface-exposed collagen. Also described are various other components which can be incorporated into the bone implant material such as bone-growth inducing substances; and a method of manufacture.

52 Claims, 5 Drawing Sheets

U.S. PATENT DOCUMENTS

| | | |
|---|---|---|
| 5,507,813 | 4/1996 | Dowd et al. . |
| 5,522,895 | 6/1996 | Mikos . |
| 5,522,904 | 6/1996 | Moran et al. . |
| 5,531,791 | 7/1996 | Wolfinbarger, Jr. . |
| 5,556,430 | 9/1996 | Gendler . |
| 5,573,771 | 11/1996 | Geistlich et al. . |
| 5,585,116 | 12/1996 | Boniface et al. . |
| 5,645,591 | 7/1997 | Kuberasampath et al. . |
| 5,683,459 | 11/1997 | Brekke . |
| 5,800,541 | 9/1998 | Rhee et al. . |

OTHER PUBLICATIONS

"Flexural Rigidity in Partially Demineralized Diaphyseal Bone Grafts", Lewandrowski et al., *Clinical Orthopaedics and Related Research*, No. 317, pp. 254–262, Lippincott—Raven Publishers (1995).

"Kinetics of cortical bone demineralization: Controlled demineralization—a new method for modifying cortical bone allografts", Lewandrowski et al., *Journal of Biomedical Materials Research*, vol. 31, pp. 365–372, John Wiley & Sons, Inc. (1996).

"Sensitivity of Osteoinductive Activity of Demineralized and Defatted Rat Femur to Temperature and Duration of Heating", Takayasu Ito, MD, et al., *Clinical Orthopaedics and Related Research*, No. 316, pp. 267–275, JB Lippincott Company, (1995).

"Radiographic Evaluation of Mandibular Augmentation With Prefabricated Hydroxylapatite/Fibrin Glue Implants", Meijer et al., *Journal of Oral and Maxillofacial Surgery*, pp. 138–145 (1997).

"Factors Affecting Bone Graft Incorporation", Stevenson et al., *Clinical Orthopaedics and Related Research*, No. 323, pp. 66–74, Lippincott—Raven Publishers (1996).

METHOD FOR AN OSTEOIMPLANT MANUFACTURE

This application is a divisional application of Ser. No. 09/020,205 filed Feb. 6, 1998, now U.S. Pat. No. 6,123,731.

BACKGROUND OF THE INVENTION

1. Field of Invention

The present invention relates to an osteoimplant for use in the repair, replacement and/or augmentation of various portions of animal or human skeletal systems and to a method for manufacturing the osteoimplant. More particularly, this invention relates to an osteoimplant made up of a solid aggregate of bone-derived elements that are bonded to each other through chemical linkages formed between their surface-exposed collagen.

2. Description of the Related Art

The use of autograft bone, allograft bone or xenograft bone is well known in both human and veterinary medicine. See Stevenson et al., *Clinical Orthopedics and Related Research*, 323, pp. 66–74 (1996). In particular, transplanted bone is known to provide support, promote healing, fill bony cavities, separate bony elements such as vertebral bodies, promote fusion and stabilize the sites of fractures. More recently, processed bone has been developed into shapes for use in new surgical applications, or as new materials for implants that were historically made of non-biologically derived materials.

U.S. Pat. No. 4,678,470 describes a non-layered bone grafting material produced from bone by a process which includes tanning with glutaraldehyde. The bone may be pulverized, used as a large block or machined into a precise shape. The tanning stabilizes the material and also renders it non-antigenic. The bone material may also be demineralized.

Collagen is a naturally occurring structural biomaterial and is a component of connective tissues, including bone, in all vertebrate species. Native collagen is a glycine-rich chain of amino acids arranged in a triple helix and can be crosslinked by a variety of procedures.

Tissue transglutaminase is described as being effective at increasing adhesive strength at a cartilage-cartilage interface. See Jurgensen, K., et al., *The Journal of Bone and Joint Surgery*, 79-A (2), 185–193 (1997).

U.S. Pat. No. 5,507,813 describes a surgically implantable sheet formed from elongate bone particles, optionally demineralized, containing biocompatible ingredients, adhesives, fillers, plasticizers etc.

U.S. Pat. No. 4,932,973 discloses an artificial organic bone matrix with holes or perforations extending into the organic bone matrix. The holes or perforations are indicated to be centers of cartilage and bone induction following implantation of the bone matrix.

U.S. Pat. No. 4,394,370 discloses a one-piece sponge-like bone graft material fabricated from fully demineralized bone powder or micro particulate bone, and reconstituted collagen. The sponge-like graft is optionally crosslinked with glutaraldehyde.

Another one-piece porous implant is described in U.S. Pat. No. 5,683,459. The implant is made up of a biodegradable polymeric macrostructure, which is structured as an interconnecting open cell meshwork, and a biodegradable polymeric microstructure composed of chemotactic ground substances such as hyaluronic acid.

SUMMARY OF THE INVENTION

The present invention provides an osteoimplant which, due to chemical linkages formed between the surface-exposed collagen of adjacent partially demineralized bone elements from which the osteoimplant is manufactured, exhibits good mechanical strength, is biocompatible and, in a preferred embodiment, through its bone healing activity and ability to contain bone-growth inducing substances, can promote and/or accelerate new bone growth.

It is therefore an object of the present invention to provide an osteoimplant made up of a solid aggregate of bone-derived elements, adjacent bone-derived elements being bonded to each other through chemical linkages between their surface-exposed collagen, and which possesses good mechanical strength and biocompatibility.

It is another object of this invention to provide an osteoimplant which can optionally include another component such as a reinforcing particle or fiber, fillers, bone-growth inducing substances such as medically/surgically useful substances, and combinations thereof.

It is another object of the invention to provide an osteoimplant possessing a network of pores, perforations, apertures, channels or spaces which permits and encourages penetration by endogenous and exogenous bone healing materials and blood supply, and simultaneously provides a means for incorporating one or more bone healing substances.

It is yet a further object of the present invention to provide an osteoimplant which can be fashioned into a variety of shapes and sizes which are not limited by constraints imposed by the size and/or types of donor bone which are available for construction of the osteoimplant.

It is also an object of the invention to provide a method of manufacturing which will provide a strong, biocompatible osteoimplant of any size and/or shape for implantation.

In keeping with these and other objects of the invention, there is provided an osteoimplant which comprises a solid aggregate of bone-derived elements with adjacent bone-derived elements being bonded to each other through chemical linkages between their surface-exposed collagen.

Further in keeping with the invention, there is provided a method for the manufacture of an osteoimplant which comprises providing a quantity of bone-derived elements presenting surface-exposed collagen and forming chemical linkages between the surface-exposed collagen to bond the elements into a solid aggregate.

The osteoimplant of the present invention possesses a significant advantage over the prior art in its ability to be biocompatible, non-antigenic and to provide good mechanical strength.

Another important advantage of the osteoimplant herein over prior art implants lies in its ability to function as a carrier for, and effectively diffuse, one or more bone-growth inducing substances that promote new bone growth and/or accelerate healing.

The term "osteogenic" as used herein shall be understood to refer to the ability of a substance to induce new bone formation via the participation of living cells from within the substance.

The term "osteoconductive" as used herein shall be understood to refer to the ability of a substance or material to provide biologically inert surfaces which are receptive to the growth of new host bone.

The term "osteoinductive" as used herein shall be understood to refer to the ability of a substance to recruit cells from the host which have the potential for repairing bone tissue.

Use of the expression "bone-derived elements" shall be understood to refer to pieces of bone in any variety of sizes, thicknesses and configurations including particles, fibers, strips, thin to thick sheets, etc., which can be obtained by milling, slicing, cutting or machining whole bone.

The expression "surface-exposed collagen" shall be understood to refer to the result obtained by demineralizing the aforementioned bone-derived elements, the demineralization ranging from substantially complete (in which case the bone-derived elements are primarily collagen) to partial or superficial (in which case only the surfaces of the bone-derived elements present exposed collagen). Partial or superficial demineralization produces bone-derived elements having a surface binding region, namely, exposed collagen while retaining a strengthening region, namely, the unaffected mineralized region of the bone-derived elements.

BRIEF DESCRIPTION OF THE DRAWINGS

Various embodiments are described below with reference to the drawings wherein.

DESCRIPTION OF THE PREFERRED EMBODIMENTS

The osteoimplant of the present invention comprises a solid aggregate of bone-derived elements having chemical linkages between their surface-exposed collagen molecules thus bonding adjacent bone elements to each other. In order to expose the collagen located on the outer surface of bone, the bone elements must be at least partially demineralized. Demineralization methods remove the mineral component of bone employing acid solutions. Such methods as used by the present invention are well known in the art, see for example, Reddi et al., *Proc. Nat. Acad. Sci.* 69, pp1601–1605 (1972), incorporated herein by reference. The strength of the acid solution, the shape of the bone and the duration of the demineralization treatment will determine the extent of demineralization. Reference in this regard may be made to Lewandrowski et al., *J. Biomed Materials Res*, 31, pp365–372 (1996), also incorporated herein by reference. The sources for the bone-derived elements herein include cortical and cancellous bone and are preferably allogenic but also include xenogenic sources such as bovine and porcine bone.

When prepared from bone-derived elements that are only superficially demineralized, the osteoimplant herein will tend to possess a fairly high compression strength, e.g., one approaching that of natural bone. Accordingly, when an osteoimplant exhibiting relatively high compression strength is desired, e.g., on the order of from about 10 to about 200 MPa, and preferably from about 20 to about 100 MPa, it is necessary to employ bone-derived elements which retain a high proportion of their original mineral content or, stated another way, which have only been superficially demineralized.

In addition to containing bone-derived elements, the osteoimplant of this invention can optionally possess one or more other components such as reinforcing particles, fibers, fillers, bone-growth inducing substances, adhesives, plasticizers, flexibilizing agents, hydration facilitating agents, biostatic/biocidal agents, substances imparting radiopacity, metallic meshes and the like. Examples of reinforcing particles include fully mineralized cortical and cancellous bone, and partially demineralized cortical and cancellous bone in any form, including particles, sheets and shaped bone pieces; graphite or pyrolytic carbon. Examples of fillers include mineral material such as hydroxyapatite, tricalcium phosphate and other calcium salts, bone powder, fully mineralized and partially or fully demineralized cortical and cancellous bone in any form, including particles such as demineralized bone powder (or "demineralized bone matrix" as it may also be called) sheets and shaped bone pieces, graphite or pyrolytic carbon, bioglass or other bioceramic or natural or synthetic polymers, e.g., bioabsorbable polymers such as polyglycolide, polylactide, glycolide-lactide copolymer, and the like, and nonbioabsorbable materials such as starches, polymethyl methacrylate, polytetrafluoroethylene, polyurethane, polyethylene and nylon. Suitable plasticizers, flexibilizing agents and hydration facilitating agents, include liquid polyhydroxy compounds such as glycerol, monacetin, diacetin, and mixtures thereof. Suitable biostatic/biocidal agents include antibiotics, povidone, sugars, and mixtures thereof; suitable surface agents include the biocompatible nonionic, cationic, anionic and amphoteric surfactants, and mixtures thereof. The osteoimplant can also possess bone-growth inducing substances which include any of a variety of medically and/or surgically useful substances which are described below.

The osteoimplant can possess one or more cavities which, if desired, can communicate with the surface of the implant through pores, apertures, perforations or channels provided for this purpose and ranging in average diameter from a few microns to several millimeters. Such cavities and their associated pores, apertures, perforations, and channels can be partially or completely filled with one or more medically/surgically useful substances which promote or accelerate new bone growth or bone healing due, e.g., to some osteogenic, osteoconductive and/or osteoconductive effect. Useful substances of this kind which can be incorporated into the osteoimplant of this invention include, e.g., collagen, insoluble collagen derivatives, etc., and soluble solids and/or liquids dissolved therein, e.g., antiviral agents, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamicin, etc.; biocidal/biostatic sugars such as dextrose, glucose, etc.; amino acids, peptides, vitamins, inorganic elements, co-factors for protein synthesis; hormones; endocrine tissue or tissue fragments; synthesizers; enzymes such as collagenase, peptidases, oxidases, etc.; polymer cell scaffolds with parenchymal cells; angiogenic drugs and polymeric carriers containing such drugs; collagen lattices; antigenic agents; cytoskeletal agents; cartilage fragments, living cells such as chondrocytes, bone marrow cells, mesenchymal stem cells, natural extracts, tissue transplants, bone, demineralized bone, autogenous tissues such as blood, serum, soft tissue, bone marrow, etc.; bioadhesives, bone morphogenic proteins (BMPs), transforming growth factor (TGF-beta), insulin-like e growth factor (IGF-1); growth hormones such as somatotropin; bone digestors; antitumor agents; immunosuppressants; angiogenic agents such as basic fibroblast growth factor (bFGF); permeation enhancers, e.g., fatty acid esters such as laureate, myristate and stearate monoesters of polyethylene glycol, enamine derivatives, alpha-keto aldehydes, etc.; and, nucleic acids. These and similar medically/surgically useful substanc es can be incorporated into the osteoimplant of this invention or any of its constituent bone-derived elements or other components during any stage of the assembly of the implant. Suitable methods of incorporation include coating, immersion saturation, packing, etc. The amounts of medically/surgically useful substances utilized can vary widely with optimum levels being readily determined in a specific case by routine experimentation.

Osteoimplants of any desirable size and/or configuration can be provided, e.g., by machining or other mechanical shaping operations such as press-molding. Computerized modeling of a specific implant followed by computerized control of the shaping of the implant can be used to provide an intricately shaped osteoimplant which is custom-fitted to the intended site of application with great precision.

Where the invention comprises aggregates of elongate bone-derived elements which, in appearance can be described as filaments, fibers, threads, slender or narrow strips, etc., an osteoimplant can be formed from these elements by a variety of methods. For example, forming a solution or slurry in a suitable medium which can comprise the crosslinking agent, and any proportion of the elongate bone-derived elements being partially or fully demineralized, and fully mineralized. This solution can be formed into an osteoimplant of any shape according to the configuration of a mold into which it is poured. The mold is preferably shaped as a bone or section thereof, or as an implant for grafting. Once contained in a mold, the solution of bone-derived elements can be solidified into a solid osteoimplant by known techniques.

It is within the scope of the invention to supplement or increase the shape-retaining and/or mechanical strength characteristics of the osteoimplant, e.g., by the addition of mechanical fasteners such as pins, screws, dowels, etc., which can be fabricated from natural or synthetic materials and bioabsorbable as well as nonbioabsorbale materials, by the use of laser tissue welding or ultrasonic bonding, and so forth. In those embodiments of the osteoimplant which are assembled from relatively large bone-derived elements such as sheets, such elements can be provided with mechanically interengaging features, e.g., tongue-and-groove or mortise-and-tenon features, which facilitate their assembly into the final product and/or to fix the elements to each other in a more secured fashion.

The osteoimplant herein is intended to be applied at a bone defect site, e.g., one resulting from injury, defect brought about during the course of surgery, infection, malignancy or developmental malformation. The osteoimplant, suitably sized and shaped as required, can be utilized as a graft or replacement in a wide variety of orthopedic, neurosurgical and oral and maxillofacial surgical procedures such as the repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery, e.g., deficit filling, discectomy, laminectomy, excision of spinal cord tumors, anterior cervical and thoracic operations, repair of spinal injuries, scoliosis, lordosis and kyphosis treatments, intermaxillary fixation of fractures, mentoplasty, temporomandibular joint replacement, alveolar ridge augmentation and reconstruction, only bone grafts, implant placement and revision, sinus lifts, etc. Specific bones which can be repaired or replaced with the osteoimplant herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal, and metatarsal bones.

The method of manufacturing the osteoimplant of the present invention comprises providing a quantity of bone-derived elements initially presenting surface-exposed collagen and subsequently forming chemical linkages between the surface-exposed collagen of adjacent bone-derived elements to bond the elements into a solid aggregate. These chemical linkages can be formed employing a variety of known methods including chemical reaction, the application of energy such as radiant energy, which includes irradiation by UV light or microwave energy, drying and/or heating and dye-mediated photo-oxidation; dehydrothermal treatment in which water is slowly removed while the bone tissue is subjected to a vacuum; and, enzymatic treatment to form chemical linkages at any collagen-collagen interface. The preferred method of forming chemical linkages is by chemical reaction.

Chemical crosslinking agents include those that contain bifunctional or multifunctional reactive groups, and which react with functional groups on amino acids such as epsilon-amine functional group of lysine or hydroxy-lysine, or the carboxyl functional groups of aspartic and glutamic acids. By reacting with multiple functional groups on the same or different collagen molecules, the reacting chemical crosslinking agent forms a reinforcing cross-bridge.

Suitable chemical crosslinking agents include: mono- and dialdehydes, including glutaraldehyde and formaldehyde; polyepoxy compounds such as glycerol polyglycidal ethers, polyethylene glycol diglycidal ethers and other polyepoxy and diepoxy glycidal ethers; tanning agents including polyvalent metallic oxides such as titanium dioxide, chromium dioxide, aluminum dioxide, zirconium salt, as well as organic tannins and other phenolic oxides derived from plants; chemicals for esterification of carboxyl groups followed by reaction with hydrazide to form activated acyl azide functionalities in the collagen; dicyclohexyl carbodiimide and its derivatives as well as other heterobifunctional crosslinking agents; hexamethylene diisocyanate; sugars, including glucose, will also crosslink collagen.

Glutaraldehyde crosslinked biomaterials have a tendency to over-calcify in the body. In this situation, should it be deemed necessary, calcification-controlling agents can be used with aldehyde crosslinking agents. These calcification-controlling agents include: dimethyl sulfoxide (DMSO), surfactants, diphosphonates, aminooleic acid, and metallic ions, for example ions of iron and aluminum. The concentrations of these calcification-controlling agents can be determined by routine experimentation by those skilled in the art.

Chemical crosslinking involves exposing the bone-derived elements presenting surface-exposed collagen to the chemical crosslinking agent, either by placing the elements in a solution of the chemical crosslinking agent, or by exposing them to the vapors of the chemical crosslinking agent under conditions appropriate for the particular type of crosslinking reaction. Such conditions include: an appropriate pH and temperature, and for times ranging from minutes to days, depending upon the level of crosslinking desired, and the activity of the chemical crosslinking agent. The osteoimplant is then washed to remove all leachable traces of the chemical.

When enzymatic treatment is employed, useful enzymes include those known in the art which are capable of catalyzing crosslinking reactions on proteins or peptides, preferably collagen molecules, e.g., transglutaminase as described in Jurgensen et al., *The Journal of Bone and Joint Surgery*, 79-A (2), 185–193 (1997), herein incorporated by reference.

Formation of chemical linkages can also be accomplished by the application of energy. One way to form chemical linkages by application of energy is to use methods known to form highly reactive oxygen ions generated from atmospheric gas, which in turn, promote oxygen crosslinks between surface-exposed collagen. Such methods include using energy in the form of ultraviolet light, microwave energy and the like. Another method utilizing the application of energy is a process known as dye-mediated photo-oxidation in which a chemical dye under the action of visible light is used to crosslink surface-exposed collagen.

Another method for the formation of chemical linkages is by dehydrothermal treatment which uses combined heat and the slow removal of water, preferably under vacuum, to achieve crosslinking of the bone-derived elements. The process involves chemically combining a hydroxy group from a functional group of one collagen molecule and a hydrogen ion from a functional group of another collagen molecule reacting to form water which is then removed resulting in the formation of a bond between the collagen molecules.

Figure 1:
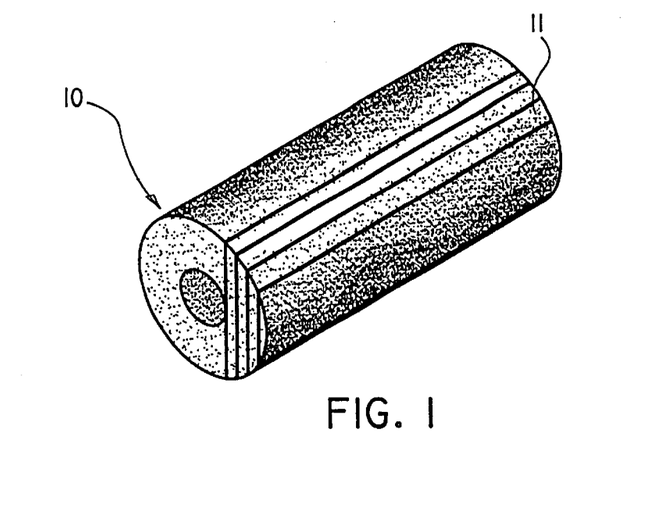
FIG. 1 is a cross-sectional view of bone from the diaphyseal region which has been sliced longitudinally into several cortical bone sheets.

Referring to the drawings, as shown in FIG. 1, the cortical portion of bone 10 taken from the diaphyseal region is cut into cortical bone sheets 11 of varying width by slicing the bone longitudinally. If desired, cortical bone sheets 11 can be further cut to uniform size and shape, as in bone-derived sheets 21 of the osteoimplant 20 shown in FIG. 2.

Figure 2:
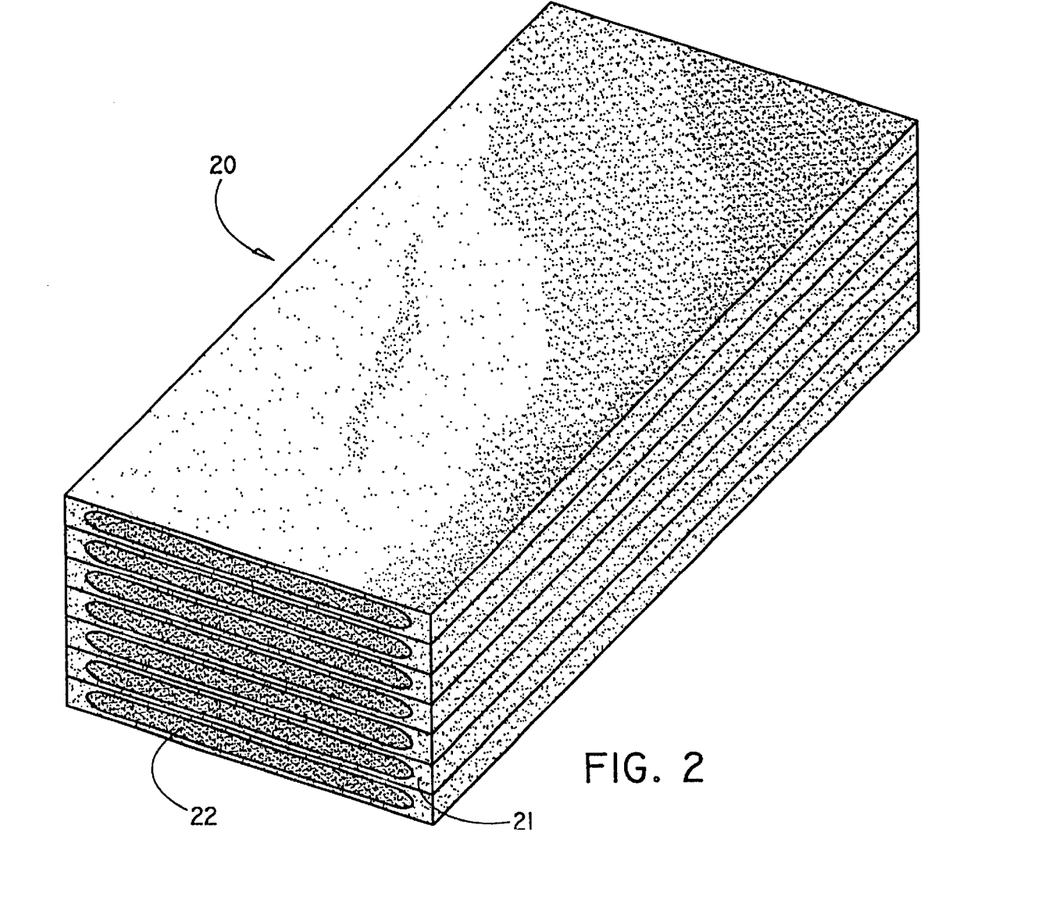
FIG. 2 is an enlarged perspective view of an osteoimplant of the invention possessing sheets of partially demineralized bone at their surface and an interior made up of mineralized or partially demineralized bone.
Figure 3:
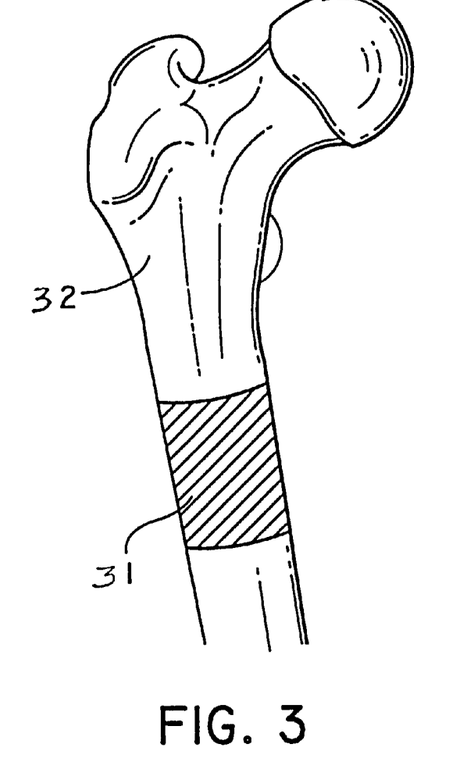
FIG. 3 is a view of a human femur showing an osteoimplant of the invention, as shown in FIG. 3A, fashioned as a femoral bone replacement.
Figure 3A:
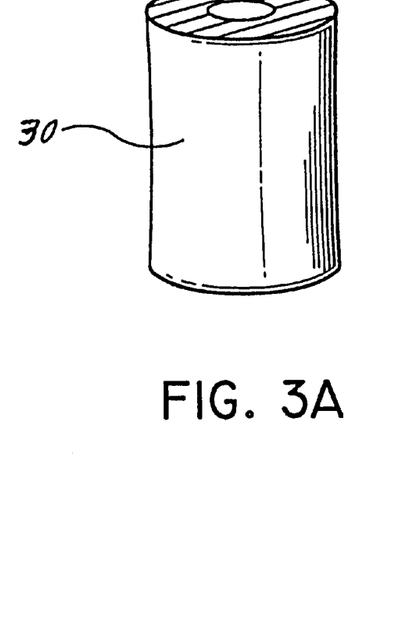

FIG. 2 illustrates an osteoimplant 20 comprising cortical bone-derived sheets 21 having a fully or partially demineralized outer surface with surface-exposed collagen, and a nondemineralized or partially demineralized core 22. Alternatively, one or more bone-derived sheets can be made from substantially completely demineralized bone. Also, another component such as demineralized bone powder can be coated on the bone-derived sheets. The entire structure has crosslinked collagen on adjacent bone-derived sheets to provide increased adhesion between them. The total thickness of the osteoimplant will ordinarily be at least about 2 to about 20 mm. Osteoimplant 20 can be cut, machined, and/or otherwise formed into any other desired shape or dimension for implantation into a body. Thus, as shown in FIG. 3A, a substantially cylindrically shaped osteoimplant 30 can be made for use as a long bone segment replacement 31 for a femur 32 of FIG. 3. To form a cylinder, a substantially square or rectangular osteoimplant can be shaped on a lathe to the required diameter. A cavity can be formed by removing bone material with, for example, a drill, or, alternatively, a cavity can be formed by assembling appropriately configured layers of bone-derived elements.

Figure 4:
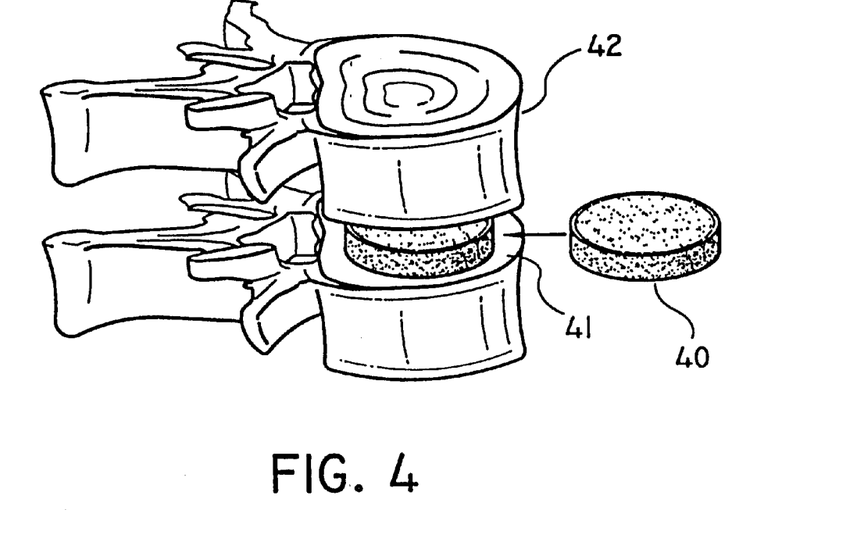
FIG. 4 is a partial view of the human vertebral column showing a disc-shaped osteoimplant of the invention installed at an intervertebral site.

As shown in FIG. 4, the disc-shaped osteoimplant 40 is shown inserted at the intervertebral fibrocartilage site 41 on the anterior side of vertebral column 42.

Figure 5:
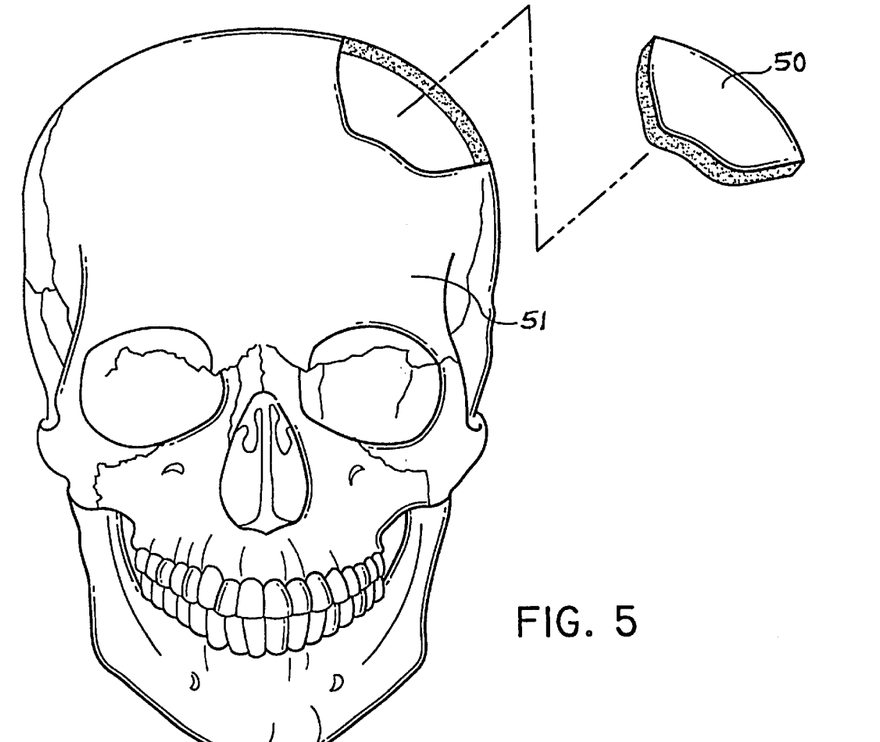
FIGS. 5 and 5A are views of a human skull showing an osteoimplant of the invention fashioned as a parietal bone replacement.
Figure 5A:
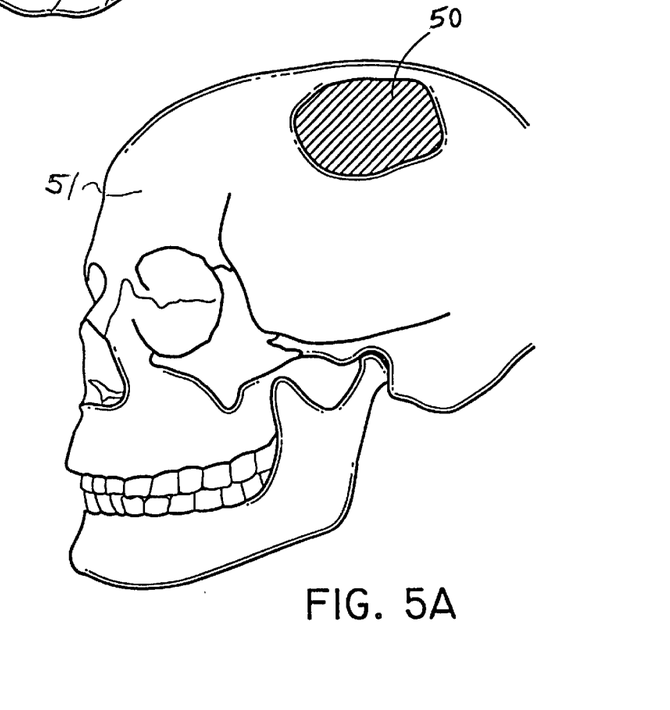

In FIG. 5, parietal osteoimplant 50 is sized and shaped to form part of the parietal bone for skull 51 in FIG. 5A.

Figure 6:
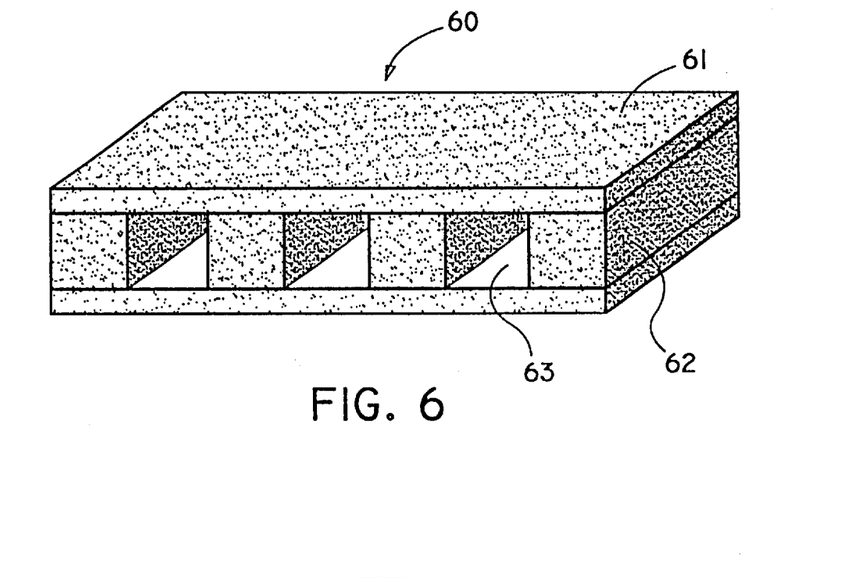
FIG. 6 is an enlarged perspective view of an osteoimplant of the invention possessing alternating layers of bone sheets and cubes with channels between the cubes.
Figure 7:
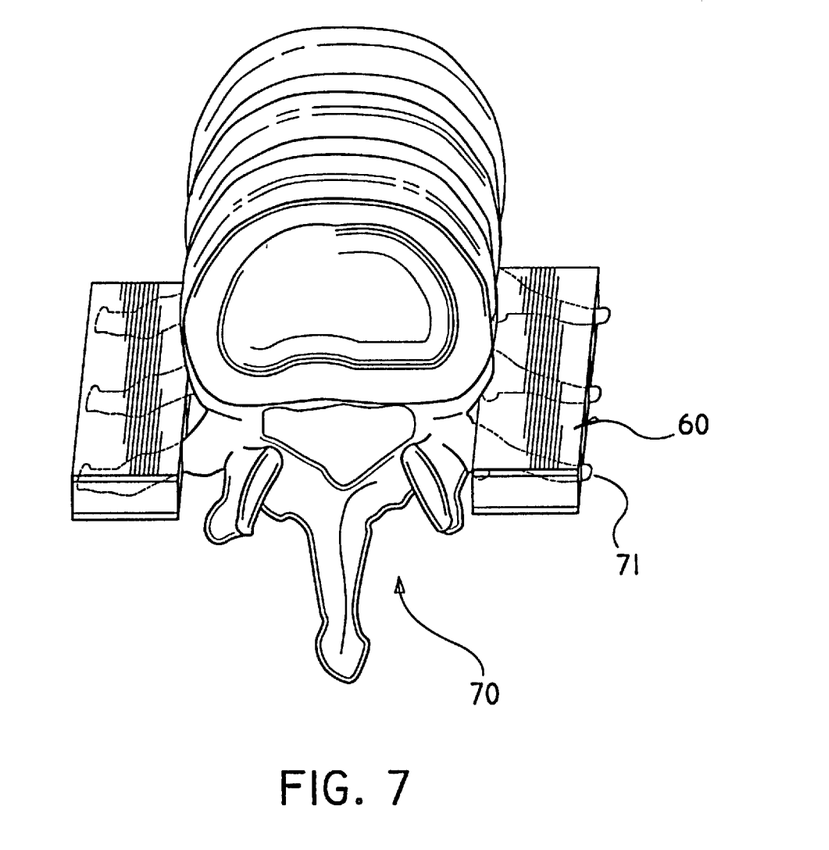
FIG. 7 is a partial view of the human vertebral column showing installation of the osteoimplant of FIG. 6 at a posterolateral intertransverse process fusion site; and, FIG. 8A is an enlarged perspective view of an osteoimplant of the invention possessing layers of bone sheets bonded together via chemical bonds formed by catalysis with tissue transglutaminase, as shown in FIG. 8.

In FIG. 6, osteoimplant 60 is built up from bone-derived sheet sections 61 of surface demineralized cortical bone, and from bone-derived cube sections 62 of surface demineralized cancellous bone of uniform, square cross section. These sheet and cube constituents are arranged in alternating layers as shown. After assembly, the structure is subjected to treatment for cross-linking. Because of the open structure of osteoimplant 60 resulting from the pattern of channels 63, the osteoimplant permits vascular penetration or host bone in growth therein and/or diffusion of one or more medically/surgical useful substances therefrom. Osteoimplant 60 is shown installed as a spinal onlay graft attached via insertion of the transverse processes 71 into channels 63, for posterolateral intertransverse process fusion on vertebral column 70 of FIG. 7.

Figures 8, 8A:
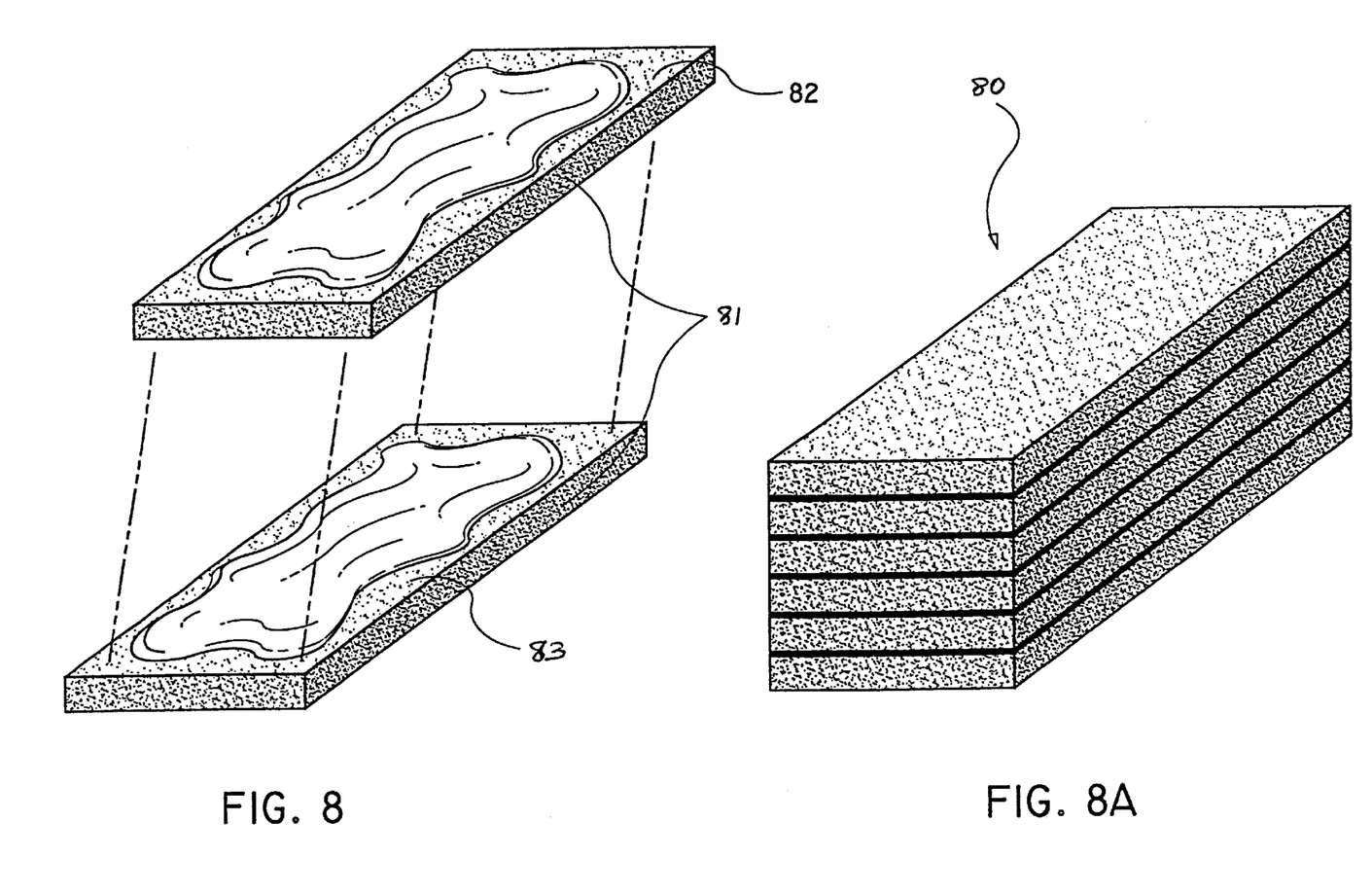

In FIG. 8A, osteoimplant 80 comprises bone-derived sheets 81 having a fully or partially demineralized outer surface. As shown in FIG. 8, a bone-derived sheet has one side coated with tissue transglutaminase 83 and, the mating surface of the adjacent sheet is coated with $CaCl_2$ 82 solution. As osteoimplant 80 is assembled, contact between the two complimentary sides of bone-derived sheets results in tissue transglutaminase 83 catalyzing collagen crosslinking at the interface of adjacent bone-derived sheets 81.

The following examples are further illustrations of the osteoimplant of this invention.

EXAMPLE 1

A cortical section of bone from the diaphyseal region was cut in the longitudinal direction while continuously wetted with water into approximately 1.5 mm thick sheets using a diamond-bladed saw. The cortical bone-derived sheets were then frozen to −70° C. and freeze-dried for 48 hours, and subsequently, were placed into excess 0.6 N HCl solution for 1.5 hours with constant stirring, washed in water for 5 minutes, and soaked for 1.5 hours in BupH phosphate buffered saline. The bone-derived sheets were assembled into a layered structure and held with a clamp. The clamped structure was then placed into a solution of 10% neutral, buffered formalin for 48 hours to crosslink the exposed collagen surfaces. After crosslinking, the clamp was removed, and the structure was placed in a container and allowed to rinse under running water for several hours. The osteoimplant was cut to shape on a band saw, and then placed in an excess aqueous solution of glycerol. After seven hours, the excess solution was removed, and the osteoimplant was freeze-dried.

EXAMPLE 2

Elongate bone-derived fibers were milled from cortical bone, and were fully demineralized in excess 0.6N HCl solution. These fibers were washed with water, and soaked in an aqueous solution of glycerol. Additionally, fully mineralized bone-derived fibers were added to the solution which was stirred and left for 12 hours at room temperature. The solution containing the soaked mineralized and demineralized bone-derived fibers were poured through a 106 micron sieve to recover the fibers. The mixture of mineralized and demineralized fibers was placed in a cylindrical die, and pressure-treated to 10,000–50,000 psi in a press for 15 minutes, and were then heated for 2 to 12 hours at 37–55 degrees C. The resulting osteoimplant pellet was freeze-dried, and placed in polyethylene glycol diglycidal ether for 12 hours at room temperature.

EXAMPLE 3

Bone-derived sheets derived from human cortical bone, approximately 1 mm thick by 7 mm wide by 50 mm long, were treated for 10 minutes in 0.6N HCl to expose surface collagen. Bone-derived cubes derived from human cancellous bone, 10 mm×10 mm, were treated to expose surface collagen at the outer borders of the cubes. All bone-derived sheets and cubes were washed in water. The pieces were assembled together with bone-derived sheets bordering the cubes, and clamped into place. The construct was then placed into a solution of 10% neutral buffered formalin for 3 hours to crosslink the surface-exposed collagen. The resulting osteoimplant was then washed in water, and cut to size on a band saw. See FIG. 6.

EXAMPLE 4

Human cortical bone-derived sheets approximately 1 mm thick were surface demineralized for 15 minutes in 0.6N HCl, then washed in running water. Tissue transglutaminase was reconstituted to give a 1 mg/ml solution. For each demineralized bone-derived sheet in the construct, the surface was blotted dry, then 40 $\mu$l/cm$^2$ area of the tissue transglutaminase was applied to one side and an equivalent volume of 0.1M CaCl$_2$ solution was applied to the mating surface of the next demineralized bone-derived sheet. This was repeated sequentially. The resulting osteoimplant was clamped and placed into a humidity chamber to promote crosslinking for approximately 30 minutes, then washed in water.

EXAMPLE 5

Cortical bone-derived sheets, approximately 2 mm thick, were surface demineralized in 0.6N HCl solution for 1 hour with constant stirring. The bone-derived sheets were then coated with dry, demineralized bone powder having a particle size of 300 microns or less, and assembled into layers. The construct was clamped into place, and placed into a solution of 10% neutral buffered formalin for 12 hours to permit collagen crosslinking. The resulting osteoimplant was washed in water to remove excess chemicals.

What is claimed is:

1. A method for the manufacture of an osteoimplant which comprises:
    a) providing a quantity of bone-derived elements initially presenting surface-exposed collagen; and,
    b) forming chemical linkages between the surface-exposed collagen of adjacent bone-derived elements to bond said elements into a solid aggregate,
    wherein chemical linkages are formed by irradiating the bone-derived elements in a gaseous environment to provide oxygen ions which thereafter react with surface-exposed collagen of adjacent bone-derived elements forming chemical linkages therebetween.

2. A method for the manufacture of an osteoimplant which comprises:
    a) providing a quantity of bone-derived elements initially presenting surface-exposed collagen; and,
    b) forming chemical linkages between the surface-exposed collagen of adjacent bone-derived elements to bond said elements into a solid aggregate,
    wherein linkages are formed by dye-mediated photo-oxidation.

3. A method for the manufacture of an osteoimplant which comprises:
    a) providing a quantity of bone-derived elements initially presenting surface-exposed collagen; and,
    b) forming chemical linkages between the surface-exposed collagen of adjacent bone-derived elements to bond said elements into a solid aggregate,
    wherein chemical linkages are formed by treating the bone-derived elements with an enzyme which catalyzes formation of chemical linkages between amino acid-functional groups of the surface-exposed collagen of adjacent bone-derived elements.

4. The method of claim 1 wherein the enzyme is a tissue transglutaminase.

5. A method for the manufacture of an osteoimplant which comprises:
    a) providing a quantity of bone-derived elements initially presenting surface-exposed collagen; and,
    b) forming chemical linkages between the surface-exposed collagen of adjacent bone-derived elements to bond said elements into a solid aggregate,
    wherein the bone-derived elements are provided with mechanically interengaging features selected from the group consisting of tongue-and-groove and mortise-and-tenon features.

6. The method of claim 1 wherein the bone-derived elements are substantially completely demineralized particles, strips or sheets of allogenic and/or xenogenic cortical bone.

7. The method of claim 1 carried out in a mold.

8. The method of claim 7 wherein the shaping surfaces of the mold are such as to provide an osteoimplant configured as a bone or section thereof.

9. The method of claim 7 wherein the shaping surfaces of the mold are such as to provide an osteoimplant configured as an intervertebral insert, a long bone, a cranial bone, a bone of the pelvis, or a bone of the hand or foot or section thereof.

10. The method of claim 1 wherein the osteoimplant possesses a compression strength of from about 10 to about 200 Mpa.

11. The method of claim 1 wherein the bone-derived elements are partially demineralized particles, strips or sheets of cortical bone.

12. The method of claim 1 wherein the bone-derived elements comprise sheets of cortical bone.

13. The method of claim 12 wherein at least one of the sheets is coated with demineralized bone powder.

14. The method of claim 12 wherein at least one of the sheets possesses a fully or partially demineralized outer surface and a nondemineralized or partially demineralized core.

15. The method of claim 12 wherein at least one of the sheets is fully demineralized.

16. The method of claim 12 wherein each sheet is approximately 1.5 mm thick.

17. The method of claim 12 wherein the sheets are assembled into a layered structure prior to forming the chemical linkages between the surface-exposed collagen of the adjacent bone-derived elements.

18. The method of claim 1 wherein the bone-derived elements are combined with at least one other component prior to forming the chemical linkages between the surface-exposed collagen of the adjacent bone-derived elements.

19. The method of claim 18 wherein the component is selected from the group consisting of reinforcing particles, reinforcing fibers, fillers, bone-growth inducing substances, growth factors, fully mineralized bone, adhesives, plasticizers, flexibilizing agents, cellular material, genetic material, calcification-controlling agents, hydration facilitating agents, biostatic agents, biocidal agents, polymers, inorganic compounds, substances imparting radiopacity and metallic meshes.

20. The method of claim 1 wherein the osteoimplant possesses pores, perforations, apertures, channels, or spheres.

21. The method of claim 20 wherein the pores, perforations, apertures, channels or spaces have incorporated therein one or more bone growth inducing or bone healing substances.

22. The method of claim 1 wherein the osteoimplant possesses a thickness of from about 2 to about 20 mm.

23. The method of claim 1 wherein the bone-derived elements comprise a mixture of fully demineralized fibers and partially demineralized fibers of cortical bone.

24. The method of claim 23 which further comprises forming the fibers into a cylindrical shape.

25. The method of claim 1 which further comprises incorporating at least one mechanical fastener to the osteoimplant.

26. The method of claim 25 wherein the mechanical fastener is selected from the group consisting of pins, screws, and dowels.

27. The method of claim 1 wherein the bone-derived elements are provided with mechanically interengaging features.

28. The method of claim 27 wherein the bone-derived elements comprise sheets of cortical bone.

29. The method of claim 1 wherein the solid aggregate is cut to provide the osteoimplant.

30. The method of claim 2 wherein the bone-derived elements are substantially completely demineralized particles, strips or sheets of allogenic and/or xenogenic cortical bone.

31. The method of claim 2 wherein the osteoimplant is configured as a bone or section thereof.

32. The method of claim 2 wherein the osteoimplant possesses a compression strength of from about 10 to about 200 Mpa.

33. The method of claim 2 wherein the bone-derived elements are partially demineralized particles, strips or sheets of cortical bone.

34. The method of claim 2 wherein the bone-derived elements are combined with at least one other component prior to forming the chemical linkages between the surface-exposed collagen of the adjacent bone-derived elements.

35. The method of claim 34 wherein the component is selected from the group consisting of reinforced particles, reinforcing fibers, fillers, bone-growth inducing substances, growth factors, fully mineralized bone, adhesives, plasticizers, flexibilizing agents, cellular material, genetic material, calcification-controlling agents, hydration facilitating agents, biostatic agents, polymers, inorganic compounds, substances imparting radiopacity and metallic meshes.

36. The method of claim 2 wherein the bone-derived elements comprise a mixture of fully demineralized fibers and partially demineralized fibers of cortical bone.

37. The method of claim 3 wherein the bone-derived elements are substantially completely demineralized particles, strips or sheets of allogenic and/or xenogenic cortical bone.

38. The method of claim 3 wherein the osteoimplant is configured as a bone or section thereof.

39. The method of claim 3 wherein the osteoimplant possesses a compression strength of from about 10 to about 200 Mpa.

40. The method of claim 3 wherein the bone-derived elements are partially demineralized particles, strips or sheets of cortical bone.

41. The method of claim 3 wherein the bone-derived elements are combined with at least one other component prior to forming the chemical linkages between the surface-exposed collagen of the adjacent bone-derived elements.

42. The method of claim 41 wherein the component is selected from the group consisting of reinforced particles, reinforcing fibers, fillers, bone-growth inducing substances, growth factors, fully mineralized bone, adhesives, plasticizers, flexibilizing agents, cellular material, genetic material, calcification-controlling agents, hydration facilitating agents, biostatic agents, polymers, inorganic compounds, substances imparting radiopacity and metallic meshes.

43. The method of claim 3 wherein the bone-derived elements comprise a mixture of fully demineralized fibers and partially demineralized fibers of cortical bone.

44. The method of claim 5 wherein the bone-derived elements are substantially completely demineralized particles, strips or sheets of allogenic and/or xenogenic cortical bone.

45. The method of claim 5 wherein the chemical linkages are formed by dehydrothermal treatment which comprises heating the bone-derived elements to remove water therefrom and removing the water.

46. The method of claim 5 wherein the osteoimplant possesses a compression strength of from about 10 to about 200 Mpa.

47. The method of claim 5 wherein the bone-derived elements are partially demineralized particles, strips or sheets of cortical bone.

48. The method of claim 5 wherein the bone-derived elements are combined with at least one other component prior to forming the chemical linkages between the surface-exposed collagen of the adjacent bone-derived elements.

49. The method of claim 48 wherein the component is selected from the group consisting of reinforced particles, reinforcing fibers, fillers, bone-growth inducing substances, growth factors, fully mineralized bone, adhesives, plasticizers, flexibilizing agents, cellular material, genetic material, calcification-controlling agents, hydration facilitating agents, biostatic agents, polymers, inorganic compounds, substances imparting radiopacity and metallic meshes.

50. The method of claim 5 wherein the osteoimplant possesses pores, perforations, apertures, channels, or spaces.

51. The method of claim 50 wherein the pores, perforations, apertures, channels or spaces have incorporated therein one or more bone growth inducing or bone healing substances.

52. The method of claim 5 wherein the bone-derived elements comprise a mixture of fully demineralized fibers and partially demineralized fibers of cortical bone.

* * * * *